US008795498B2

(12) United States Patent
Toomey et al.

(10) Patent No.: US 8,795,498 B2
(45) Date of Patent: Aug. 5, 2014

(54) MICROBIAL CELL AND PARTICLE SELECTION SYSTEM AND METHOD OF USE

(71) Applicants: Ryan Toomey, Tampa, FL (US); Peter George Stroot, Parker, CO (US)

(72) Inventors: Ryan Toomey, Tampa, FL (US); Peter George Stroot, Parker, CO (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/056,655

(22) Filed: Oct. 17, 2013

(65) Prior Publication Data

US 2014/0093933 A1 Apr. 3, 2014

Related U.S. Application Data

(63) Continuation of application No. 11/735,743, filed on Apr. 16, 2007.

(60) Provisional application No. 60/744,883, filed on Apr. 14, 2006.

(51) Int. Cl.
*B03C 5/00* (2006.01)

(52) U.S. Cl.
USPC .... 204/547; 204/571; 210/748.01; 435/173.9

(58) Field of Classification Search
None
See application file for complete search history.

(56) References Cited

U.S. PATENT DOCUMENTS

| 6,491,061 | B1 * | 12/2002 | Lopez et al. | 137/599.01 |
| 2001/0045359 | A1 | 11/2001 | Cheng et al. | |
| 2003/0157587 | A1 | 8/2003 | Gomez et al. | |
| 2004/0026250 | A1 * | 2/2004 | Cummings et al. | 204/547 |
| 2005/0175981 | A1 | 8/2005 | Voldman et al. | |

OTHER PUBLICATIONS

Dogu, Y et al. Swelling-deswelling kinectics of poly(N-isopropylacrylamide) hydrogels formed in PEG solutions. Journal of Applied Polymer Science. 2006. Published online Oct. 11, 2005. 99(1): 37-44.*
Woese, C.R. and G.E. Fox, Phylogenetic structure of the prokaryotic domain: the primary kingdoms. Proc. Natl. Acad. Sci. USA, 1977. 74: p. 5088-5090.
Hugenholtz, P., Exploring prokaryotic diversity in the genomic era. Genome Biol, 2002. 3(2): p. 0003.1-0003.8.
Castellanos, A., S.J. Dupont, August J. Heim II, Garrett Matthews, P.G. Stroot, W. Moreno, R. Toomey (2007) "Size-Exclusion "Capture and Release" Separations using Surface-Patterned Poly(N-isopropylacrylamide) Hydrogels" Langmuir 23(11): 6391-5.
Yu, C. et al. 2003. "Flow Control Valves for Analytical Microfluidic Chips without Mechanical Parts Based on Thermally Responsive Monolithic Polymers." Analytical Chemistry. vol. 75, No. 8, pp. 1958-1961.

* cited by examiner

*Primary Examiner* — Allison Ford
*Assistant Examiner* — Susan E Fernandez
(74) *Attorney, Agent, or Firm* — Michele L. Lawson; Smith & Hopen, P. A.

(57) ABSTRACT

The invention comprises two key components: dielectrophoresis (DEP) and reversible binding surfaces. DEP has become an important tool for trapping dielectric particles. Moreover, DEP can manipulate cell movement as dictated by the intrinsic dielectric constant of the cell without modification. DEP therefore provides a mechanism by which to force targets in a flow channel to a reversible binding surface. By building selectivity into the binding surface, the capacity to choose which targets can be held after the dielectric field is turned off, providing a separation strategy that does not suffer from fouling issues, as large foulants can freely pass over the surface through the flow channel.

9 Claims, 12 Drawing Sheets

Before current applied      After current applied

MICROBIAL CELL AND PARTICLE SELECTION SYSTEM AND METHOD OF USE

CROSS REFERENCE TO RELATED APPLICATIONS

This application claims priority to currently pending U.S. patent application Ser. No. 11/735,743, entitled "Microbial Cell and particle Control", filed Apr. 16, 2007, which claims priority to U.S. Provisional Patent Application 60/744,883, entitled "Microbial Cell Control" filed Apr. 14, 2006, the contents of each of which are herein incorporated by reference.

FIELD OF INVENTION

This invention relates to a microbial cell control system that can separate cells of various types. This technology can also be extended to separate micro and nanoscale particles within a bin or range of predefined sizes.

BACKGROUND OF THE INVENTION

The separation, manipulation and sorting of biological components is essential to the success of microfluidic and other portable diagnostics. Current needs in the areas of low cost battlefield diagnosis and homeland security requires robust and inexpensive platforms that combine sample processing, detection, and signal transduction into an integrated package. These diagnostic sensors must satisfy three major criteria: low power, little skills training for the end-user and the ability to directly sample "dirty" environments or complex matrices.

Sample processing of complex matrices, however, remains the limiting factor in any portable device. An onboard process must be established that ensures both the sample purity and sample concentration are high enough to guarantee detection success. Current "macroscopic" or laboratory solutions, including electrokinetics, flow cytometry, centrifuging, and hydrodynamic sorting are not suitable for portable devices. Furthermore "microscopic" solutions including magnetic activated or fluorescent activated cell sorting require relatively pure samples and a hybridization step, which limits throughput capacity and response time.

Membrane Bioreactors enrich too many cell types and are prone to biofouling. Membranes provide environmental engineers with the ability to prevent the removal of all microbial cells. While this approach is advantageous because it allows for the enrichment of slowly growing microbes with specialized metabolic functions (ex. Methanogens), these systems suffer from three problems:

1) Enrichment of contaminants, such as filamentous bacteria that can cause foaming of the biosolids. This foaming can result in loss of biosolids with subsequent poor performance.

2) Enrichment of all cell types results in high levels of biomass, which is difficult to mix and/or aerate.

3) The membranes are also prone to biofouling which require higher pressures to move liquid across the membrane. Membranes are typically cleaned with harsh chemicals or simply replaced.

Before the 1970's the phylogeny of the Prokaryotes was based on crude comparisons of morphology and pattern of substrate utilization and was largely ignored due to the presumed simplicity of the organisms. Carl Woese used a different strategy to tackle Prokaryotic phylogeny. He focused on sequence comparisons of the ribosome, which is a biomolecule found in all life forms. The ribosome is an essential macromolecule that is involved in the translation of messenger RNA into proteins. Woese argued that since protein synthesis is an essential function for life, the ribosome could not withstand major sequence changes or life would cease. He then targeted one molecule, the 16S rRNA of Prokaryotes and the analogous 18S rRNA for Eukaryotes, and did comparisons by sequence analysis [1]. A new phylogeny of all life was discovered and to his surprise (and other biologists), the old phylogeny of Eukaryotes and Prokaryotes was discarded for a three-kingdom version that included Bacteria, Archaea, and Eucarya.

Over time, most biologists have accepted this paradigm shift. To date, 35 Bacteria phyla and 18 Archaea phyla were identified, despite only having 30 cultivatable representatives for both [2]. The branch lengths of the major Bacteria groups suggest significant differences in the genetic makeup and phenotypic characteristics. For example, the Gram positive bacteria form a distinctive phylogenetic group and have a distinctly different cell wall compared to the rest of the bacteria, which are Gram negative. Each of these major groups of Bacteria has gross differences in their surface properties that can be exploited by the present invention.

SUMMARY OF INVENTION

The present invention deals directly with the issue of "sample purification" with an integrated device that provides simultaneous concentration of a biological target and the removal of background interferences that could jeopardize any subsequent detection step. The purification process forgoes the use of an antibody-based separation, which would limit shelf life and still not guarantee selective depletion of the target from a dirty or crowded background.

The invention comprises two key components: dielectrophoresis (DEP) and reversible binding surfaces. DEP has become an important tool for trapping dielectric particles. Moreover, DEP can manipulate cell movement as dictated by the intrinsic dielectric constant of the cell without modification. DEP therefore provides a mechanism by which to force targets in a flow channel to a reversible binding surface. By building selectivity into the binding surface, the capacity to choose which targets can be held after the dielectric field is turned off provides a separation strategy that does not suffer from fouling issues as large foulants can freely pass over the surface through the flow channel.

The present invention includes control of microbial cells by forcing targets in a flow channel by dielectrophoresis to a reversible binding surface. Flow velocity is adjusted according to a preselected value. This preselected value for *E. coli* under the conditions of the inventors' experiments is a flow velocity between 0.5 and 2 centimeters per second or that which achieves laminar flow conditions. In addition, the temperature of the targets and/or binding surface may be elevated to a preselected value. In an embodiment of the invention both temperature and flow velocity are concurrently adjusted to preselected values.

An array of known microbial cell types are subjected to a plurality of temperatures and flow velocities thereby establishing an optimum temperature and flow velocity for each known microbial cell type. A target microbial cell type is then selectively separated from an unknown sample by subjecting the sample to the corresponding optimum temperature and flow velocity for the target microbial cell type.

The reversible binding surface is fabricated from a lower critical solution temperature polymer such as N-isopropylacrylamide and may optionally have size-exclusion trenches patterned into the binding surface.

Size-exclusion based separations can be performed for the capture and release of micro/nano-scale particles by patterning a stimuli responsive polymer (SRP) in the form of high aspect ratio monoliths forming a series of trenches. Volume-phase shifts in the polymer network due to external stimuli cause the surface bound high aspect ratio trenches to open and close. If the monoliths, which become the trench walls, are properly spaced the high aspect ratio trenches do not fully close upon stimulation resulting in a gap which is significantly smaller than the trench gap in the original state. This allows for the capture of a bin or range of particle sizes. Particles which are smaller than the opened trench width are captured by movement of particles to the network surface by DEP. The stimulus is applied (for example, thermal actuation) capturing all particles smaller than the opened trench width. When the trench is closed a gap with predetermined dimension is formed which allows the removal of particles smaller than the gap by reversing the DEP field. The work which demonstrates the size-exclusion based separation capability of these networks was previously described in publication.

Thus, an embodiment of the invention includes size-exclusion based separation of a bin of particle sizes wherein high aspect ratio monoliths are patterned in series to form a polymer trench network of trenches. The trench network is opened and closed by thermal adjustment achieved by applying temperatures of about 38° C. for opening the trench network and about 22° C. for closing the trench network. Dielectrophoresis is used to move particles to a surface of the trench network and spacing of the series of high aspect ratio monoliths produce a tunable gap which provides a lower-scale separation parameter making separation capabilities analogous to a band-pass filter. Reversal of the dielectrophoresis field after trench network closing results in the removal and exclusion of the lower-scale particles which have previously been entrapped.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
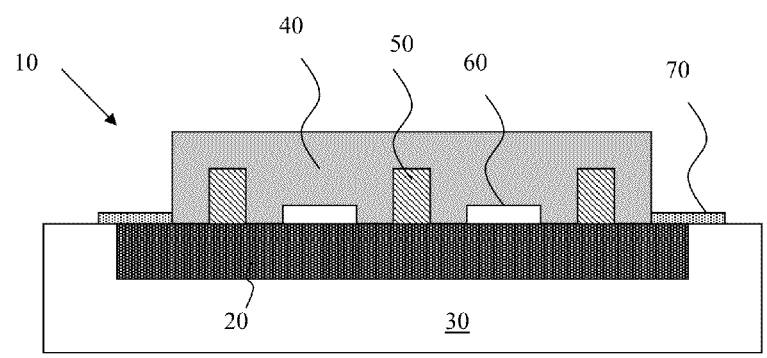
FIG. 1 is diagrammatic cross-sectional view of an embodiment of a cell control system according to the invention.

Referring to FIG. 1, a microbial cell control system 10 in accordance with an embodiment of the present invention is illustrated having a heating element 20 embedded within a silicone substrate 30. A microfluidic channel 40 is on top of the heating element 20. Contained within the microfluidic channel 20 are a reversible binding surface 50 (RBS), formed of the lower critical solution temperature (LCST) N-Isopropylacrylamide (NIPPAm) and a DEP microelectrode array 60 which are arranged on top of the heating element 20.

The reversible binding surfaces are fabricated from a lower critical solution temperature (LCST) polymer called N-Isopropylacrylamide or NIPPAm, which experiences remarkable hydration-dehydration in response to relatively small changes in temperature. At a temperature below the LCST, the surfaces hydrate and form a "repellent" surface. When the temperature exceeds LCST, chains dehydrate to form an "attractive surface" where debris, targets, and other background are bound. These bound objects can be selectively removed from the surfaces following switching off of the dielectric field through one of three mechanisms:

1) changes in flow stress on the particle;
2) changes in the binding affinity of the surface as controlled by temperature;
3) size-exclusion "trenches" can be patterned into the binding surfaces which permit the passage of the small sized particles into the membrane, which can then be held after the field is turned off.

Experimental results described below provide evidence that the dielectrophoresis and responsive surface components are enabled under the present invention.

Dielectrophoresis Experiment

Figure 2:
FIG. 2 is an array of images showing the movement of cells as a result of dielectrophoresis.
Figure 2:

E. coli GFP is moved rapidly to the surface as a result of dielectrophoresis. The two images in FIG. 2 demonstrate that we can move cells of E. coli GFP rapidly from solution to the surface of electrodes.

Materials and Methods

Two silicon chips were prepared with several spots of membrane/solvent on each. These chips were rinsed with RO/DI water and allowed to dry. In preparation for the experiment, a hybridization oven and water bath were both set to 38°

C. One of the chips was placed in the oven, while the other was left out at room temperature (22° C.). A 50 ml conical tube of rinse water (RO/DI) was placed in the water bath, and another was left at room temperature. Two cultures of E. coli w/green fluorescent protein (GFP) were prepared and allowed to equilibrate at the two operating temperatures. The cultures were prepared as follows:

1. A single colony of E. coli w/GFP was added to 1 ml of minimal media and resuspended by vortex
2. The culture (0.5 ml) was added to two tubes containing 1.5 ml of minimal media
3. Each of the two cultures were mixed by vortex and allowed to equilibrate at the two defined temperatures.

Once the components were equilibrated at the defined temperatures, the cultures were transferred by pipette to the membrane spots on each chip. One spot was left dry on each chip for comparison purposes. Each chip was hybridized for five minutes and then rinsed in their respective rinse water tubes. Each chip was submerged into the tube for ten seconds, and then removed for ten seconds. The water velocity relative to the chip was 0.56 cm/s (Re 1,288, which is laminar flow). Following the rinse, the chips were given a quick shake to remove the excess surface moisture.

The chips were analyzed by epifluorescence microscopy and images were collected at a magnification of 250× using a FITC filter cube.

Results

Figure 3:
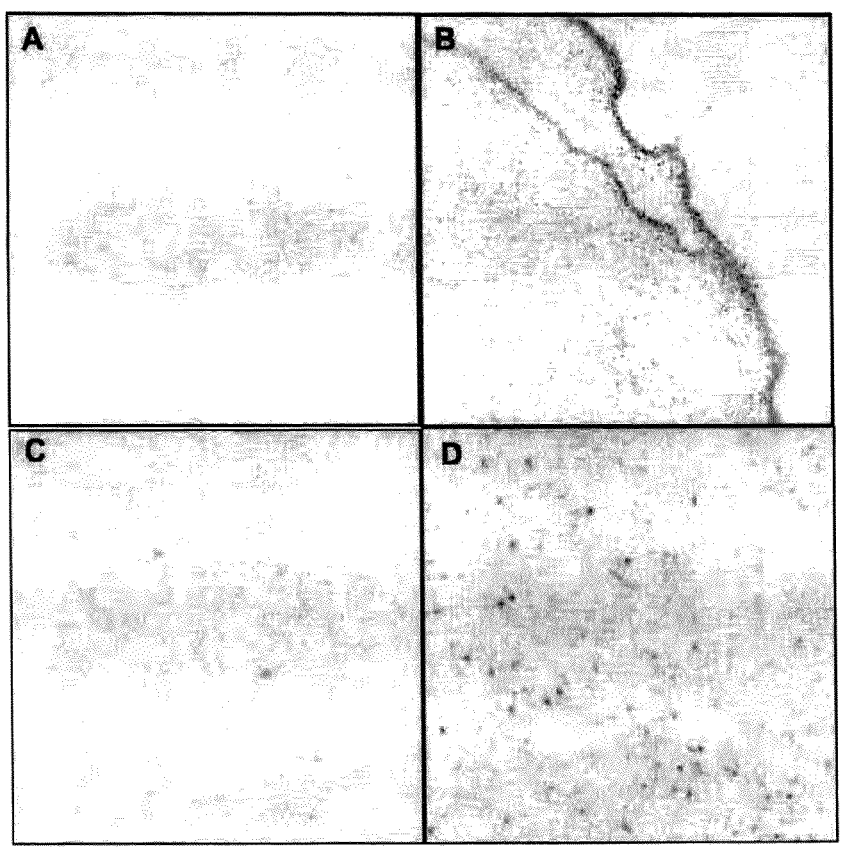
FIG. 3 is an array of images showing comparative hybridization in varying temperatures.

Representative images from the microscopic analysis are shown in FIG. 3. The images correspond to: (A, C) membrane area hybridized for 5 minutes and rinsed at 22° C., and (B, D) membrane area hybridized for 5 minutes and rinsed at 38° C. Magnified images are provided (C, D). Based upon the images in FIG. 3 it can be concluded that the bacteria successfully attached to the membrane at 38° C., but not at 22° C. There were a small number of cells that attached to the membrane at 22° C.

Responsive Surface Experiment #2

E. coli GFP adheres to the responsive surface at low fluid velocities with temperatures greater than the LCST.

Purpose of experiment: To determine the water velocity that removes the E. coli GFP cells from the responsive membrane when the temperature remains constant and above LCST.

Materials & Methods: Several silicon slides treated with the membrane material have been fabricated. Each slide has a few spots of the membrane. The biological sample is E. coli with green fluorescent protein (GFP).

All samples are kept at a temperature of 38° C. Slides were placed in a hybridization oven and allowed to equilibrate (about 10 minutes). Approximately 200 µl of resuspended E. coli (w/GFP) was placed on each spot on the slides. The slides were allowed to hybridize for another 5 minutes. Once complete, the slides were lowered individually into RO water (at 38° C.) in the times shown in Table 1. They were then pulled up in the water in the same amount of time. These "down then up" cycles were repeated five times for each slide.

TABLE 1

Data from dip experiment

| Slide Number | Dip Time (seconds) | Total time in water (sec) | Estimated Velocity (cm/s) | Reynolds Number | Estimated cells remaining (%) |
|---|---|---|---|---|---|
| 1 | 10 | 100 | 0.56 cm/s | 1,288 | 100 |
| 2 | 5 | 50 | 1.12 cm/s | 2,576 | 10 |
| 3 | 2 | 20 | 2.8 cm/s | 4,293 | 3 |
| 4 | 1 | 10 | 3.73 cm/s | 8,587 | <1 |

Figure 4:
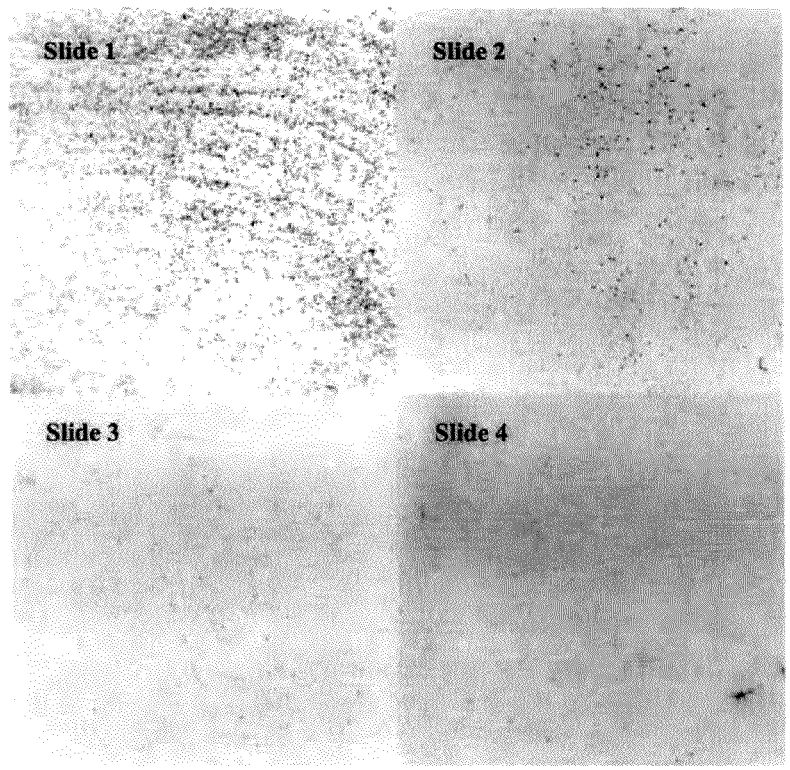
FIG. 4 is an array of slide images showing comparative hybridization at varying flow rates.

After each slide was dipped, they were allowed to dry in the hybridization oven (about 5 minutes) and subjected to image analysis. The images taken are shown in FIG. 4 wherein the spots are E. coli GFP cells.

Capture and Release, Size-Based Exclusion Separation Experiment

Figure 6:
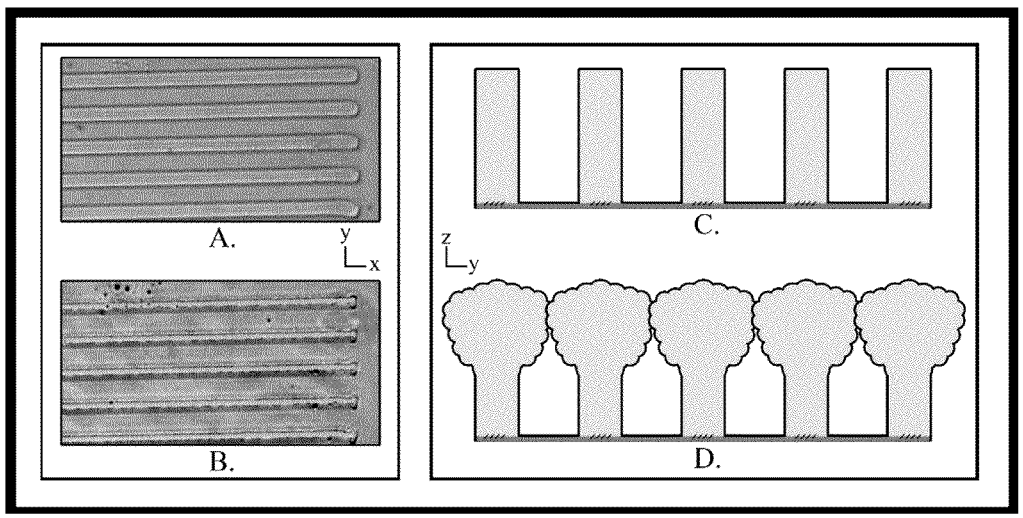
FIGS. 6A-B are bright field images taken at 25× magnification of the high aspect ratio monolithic trench network.
FIGS. 6C-D are conceptualizations of the trench network's cross section according to an embodiment of the invention.

Additionally, when the NIPAAm surface is patterned on a substrate surface in the form of long, high aspect ratio monoliths size-exclusion based separations are possible. Thermal actuation of high aspect ratio patterned monoliths of poly-N-isopropylacrylamide was demonstrated by opening and closing of the trench network by adjusting fluid temperatures from 40° C. to 25° C. as shown in FIG. 6. FIGS. 6A-B are bright field images taken at 25× magnification of the high aspect ratio monolithic trench network (A) in its opened state (at temperatures above the network's LCST) and (B) in its closed state (at temperatures below the network's LCST) and conceptualization of the trench network's cross section in it's opened (C) and closed (D) state.

Figure 7:
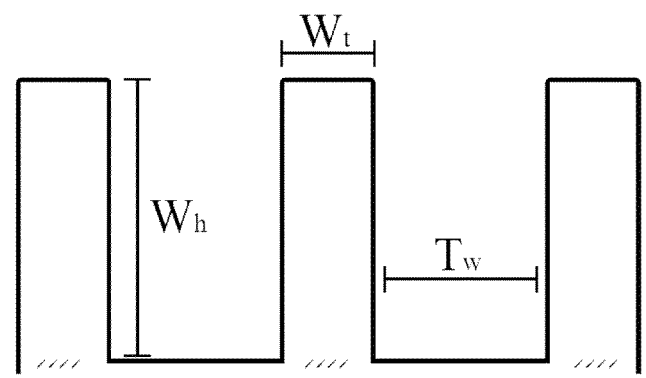
FIG. 7 is a diagrammatic view of the geometric parameters for the prediction of the size-exclusion gap ($G_W$) and the height of the newly formed channel ($T_H$) as a function of the fabrication geometry: trench wall height ($W_H$), trench wall thickness ($W_t$), and trench width ($T_W$).
Figure 7:
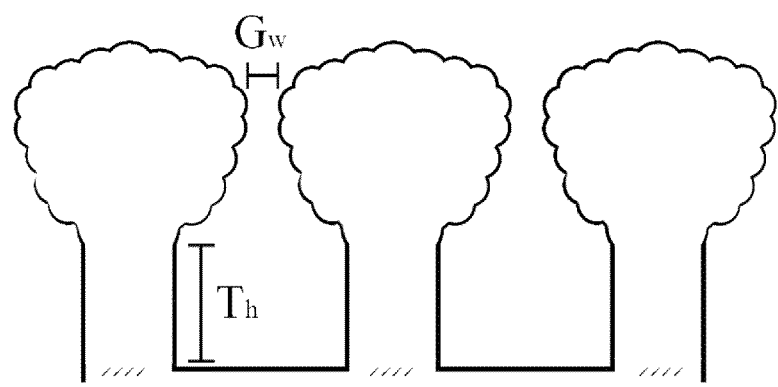
Figure 8:
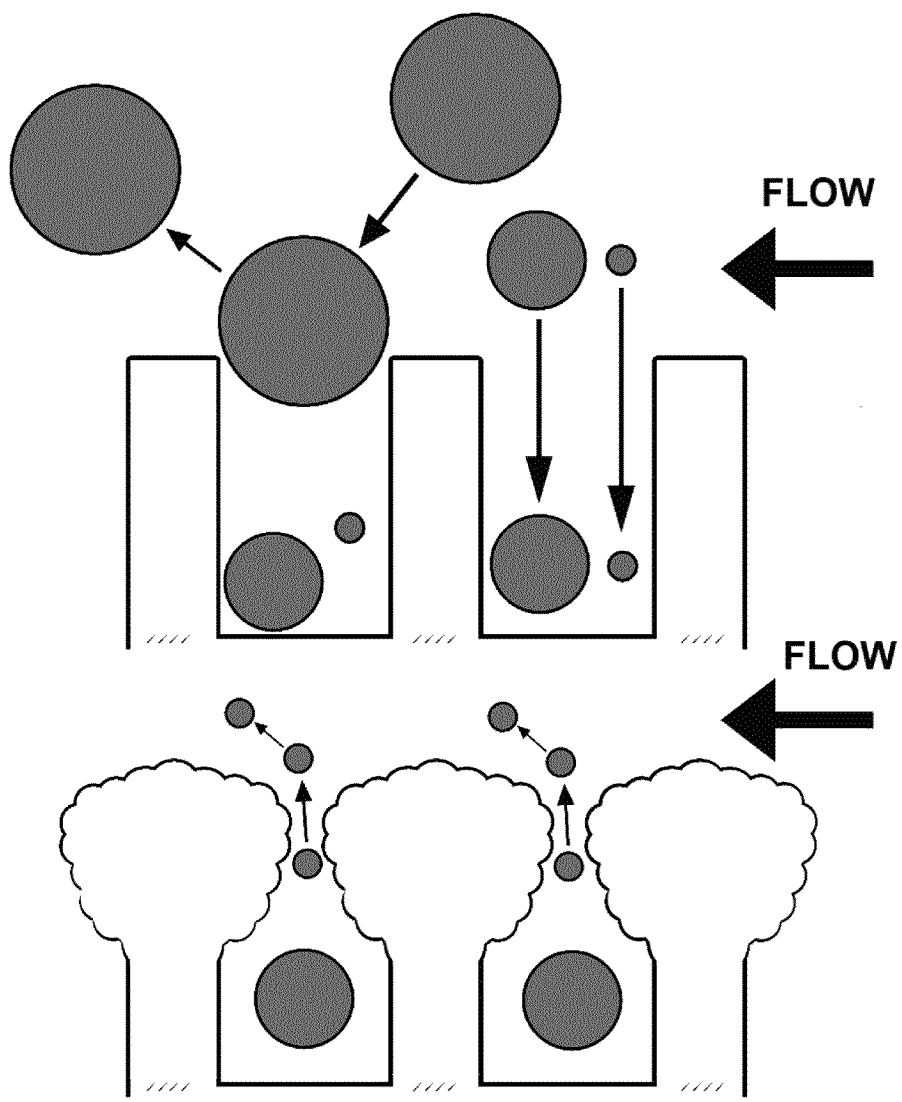
FIG. 8 is a conceptual demonstration of the capture of a medium sized particle by exclusion of both large and small particles. As shown in the Figure, when particles of different sizes are flowed over the trench network with the tunable gap in the open position, small and medium sized particles enter the trench system while large sized particles are excluded due to their size. When the trenches are closed and the DEP field is reversed, medium sized particles are trapped within the trench network while small sized particles are able to exit the trenches through the tunable gap. As a result, only medium sized particles are captured.

Notice the incomplete closing of the trench network in panel B of FIG. 6. This gap generated by the incomplete closing of the network can be employed for additional separation versatility by allowing for the capture of a bin of particles mid-range of the entire range of available particles. As shown in FIG. 7, the gap generated by the network's incomplete closing can be predicted by analyzing the swelling characteristics of the SRP used.

Figure 9:
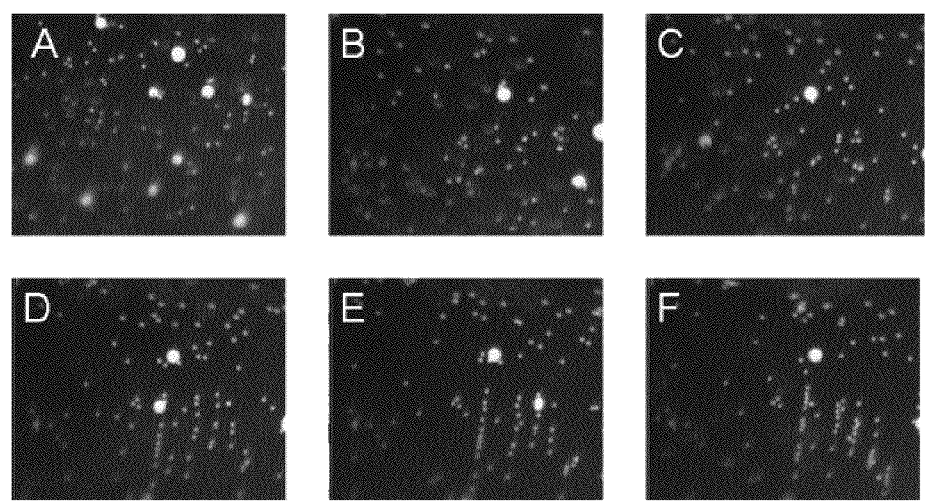
FIG. 9 demonstrates microsphere accumulation between the poly-NIPAAm hydrogel monoliths at temperatures above the LCST. The first panel (A) denotes the initial time with subsequent panels corresponding to increasing time. The gap between the monoliths is 12 μm and therefore only the small (6 μm) microspheres accumulate. The large (20) μm spheres are excluded from accumulation.
Figure 10:
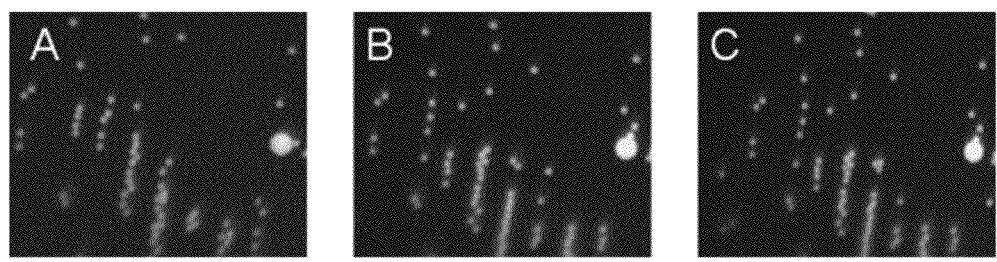
FIG. 10 is a time series of images showing the alignment of captured microspheres (6 μm) in the trenches as temperature is reduced from 40° C. (frame A) to 25° C. (frame C).
Figure 11:
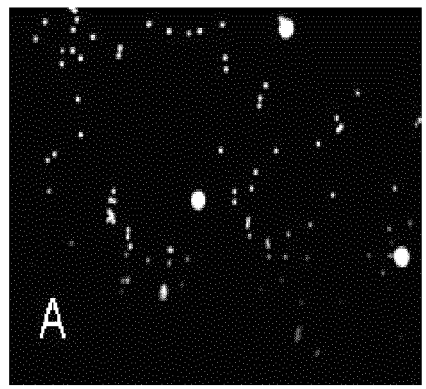
FIG. 11 shows the release of the 6 μm microspheres at elevated temperature. Shortly after the temperature is increased, the microspheres lose their alignment and leave the trenches (A). After longer incubation times, most of the microspheres are released (B).
Figure 11:
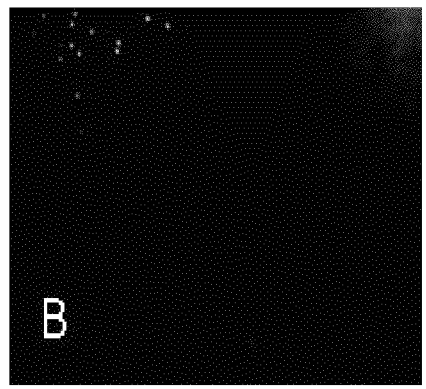
Figure 12:
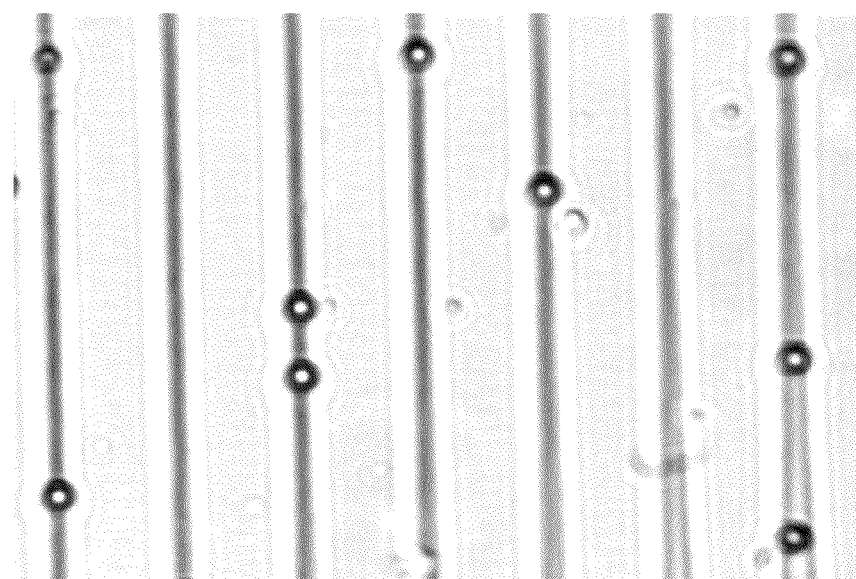
FIG. 12 shows microspheres entrenched in the high aspect ratio monoliths of p-NIPAAm

Size-exclusion separation of 6 µm microspheres from a mixture of 6 µm and 20 µm microspheres was demonstrated. A P-NIPAAm trench network was covalently bound to a glass surface within the microfluidic channel. The trench monoliths were spaced 12 µm apart resulting in the exclusion of the 20 µm microspheres. This was accomplished by flowing a solution of the microsphere mix to the microfluidic device. DEP was used to drive the particles to the trench network surface and thermal actuation (closing) of the trench network was facilitated by adjusting the fluid temperature below the polymer's LCST (32° C.). This resulted in the entrapment of 6 µm spheres and exclusion of the 20 µm spheres due to the spacing of the monoliths as demonstrated in FIGS. 9 and 10. The entrapped microspheres were then released by increasing fluid temperature above the polymer's LCST as shown in FIG. 11.

Conclusions

Figure 5:
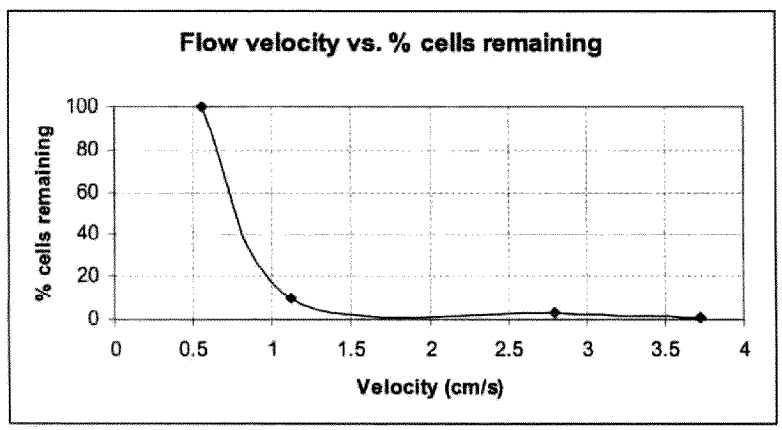
FIG. 5 is a plot of water velocity's effect on cell hybridization to a membrane.

Based upon the images shown in FIG. 4, it is apparent that the water velocity has an effect on the ability of the membrane to hold the cells. FIG. 5 shows a plot of the velocity vs. cells remaining. It is obvious that there is a rapid sloughing effect as the flow velocity increases from 0.56 cm/s. This velocity represents a Reynolds Number (Re) of 1,288, which is well into the laminar range. Based upon this preliminary data, it appears that the cells are able to stay attached to the membrane for laminar flow conditions, but not so for turbulent flow conditions.

REFERENCES

The following citations are incorporated herein by reference:
1) Woese, C. R. and G. E. Fox, Phylogenetic structure of the prokaryotic domain: the primary kingdoms. Proc. Natl. Acad. Sci. USA, 1977. 74: p. 5088-5090.
2) Hugenholtz, P., Exploring prokaryotic diversity in the genomic era. Genome Biol, 2002. 3(2): p. RE VIE WS0003.
3) Castellanos, A., S. J. DuPont, August J. Heim II, Garrett Matthews, P. G. Stroot, W.
Moreno, R. Toomey (2007) "Size-Exclusion "Capture and Release" Separations using Surface-Patterned Poly(N-isopropylacrylamide) Hydrogels" *Langmuir* (advanced online publication)

The disclosure of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of size-exclusion based separation of a bin of particle sizes using a cross-flow system comprising:
   flowing particles of interest using dielectrophoresis in a cross-flow orientation over a polymer trench network of high aspect ratio hydrogel monoliths attached to a solid surface and patterned in series to form the trench network wherein the trench network is comprised of a reversible binding surface;
   spacing the high aspect ratio hydrogel monoliths to produce a tunable gap for the size-exclusion based separation wherein the tunable gap is a function of trench wall height, trench wall thickness, and trench width; and
   adjusting the temperature of the polymer trench network above or below a critical solution temperature to control the opening of the trench network to trap at least one of the particles of interest in the trench network;
   whereby adjusting the temperature below the critical solution temperature of the polymer used in the polymer trench network closes the network by causing the hydrogel monoliths to swell parallel to the solid surface thus trapping lower scale particles in the trench network and adjusting the temperature above the critical solution temperature of the polymer opens the network releasing the previously trapped particles.

2. The method of claim 1, wherein thermal adjustment is achieved by applying temperatures of about 38° C. for opening the trench network and about 22° C. for closing the trench network.

3. The method of claim 1, wherein the tunable gap provides a lower-scale separation parameter making separation capabilities analogous to a band-pass filter.

4. The method of claim 1, wherein reversal of the dielectrophoresis field after trench network closing results in the removal and exclusion of the lower-scale particles which have previously been entrapped.

5. The method of claim 1, further comprising adjusting flow velocity according to a preselected value.

6. The method of claim 5, wherein the flow velocity is between about 0.5 and 2 centimeters per second.

7. The method of claim 5, wherein the flow velocity is adjusted to achieve laminar flow conditions.

8. The method of claim 1, wherein the reversible binding surface is fabricated from a lower critical solution temperature polymer.

9. The method of claim 8, wherein the polymer is N-isopropylacrylamide.

\* \* \* \* \*